US00PP08154P

United States Patent [19]

Austin

[11] Patent Number: Plant 8,154

[45] Date of Patent: Feb. 23, 1993

[54] ROSE PLANT—'AUSCRIM'

[75] Inventor: David C. H. Austin, Albrighton, England

[73] Assignee: David Austin Roses, Albrighton, England

[21] Appl. No.: 623,288

[22] Filed: Dec. 6, 1990

[51] Int. Cl.[5] ..... A01H 5/00

[52] U.S. Cl. ..... Plt./1

[58] Field of Search ..... Plt./1

*Primary Examiner*—Howard J. Locker

*Attorney, Agent, or Firm*—Ladas & Parry

[57] ABSTRACT

A new variety of rose plant of the shrub class distinctive in its character by its fully double, scarlet/deep red flowers with abundant continual blooming, and the unusual shaping of the flowers.

1 Drawing Sheet

BACKGROUND OF THE INVENTION

The present invention relates to a new and distinct variety of shrub roses, said new variety originating as a single seedling resulting from a definite effort to produce an improvement in this class of rose.

BRIEF SUMMARY OF THE INVENTION

Primary features of this new variety which connote a distinctive advance over existing types are the vigorous abundant and continual blooming that occurs for 5 months taken with the perfection of the fully double flowers of an old-fashioned shape, more particularly apparent in the accompanying illustration of a specimen thereof.

BRIEF DESCRIPTION OF THE DRAWING

BRIEF DESCRIPTION OF THE DRAWING

The accompanying illustration shows typical cultivar flowers of this new cultivar in various stages of development, depicted in color as nearly true as is possible to make the same in color illustrations of this character.

DETAILED BOTANICAL DESCRIPTION

The following is a detailed description of the new variety, color terminology being in accordance with the "Methuen Handbook of Color" published by Eyre Methuen Ltd (1963).

Variety denomination (in accordance with the UPOV Convention): Auscrim.

Cultivar *TRADE NAME:* L. D. Braithwaite.

Type.—Hardy, bush, outdoor, seedling, cut flowers, garden decoration.

*Class.*—Shrub.

Propagation: The variety holds its distinguishing characteristics through succeeding propagations by budding.

Asexual reproduction of the new cultivar by budding has taken place at a nursery in Albrighton, Nr. Wolverhampton, England and was derived as follows:

Female parent (seed parent): Mary Rose (non-patented).

Male parent (pollen parent): The Squire (non-patented).

The operation of the artificial pollination is therefore expressed by the following: Mary Rose×The Squire.

The following observations are made of specimens grown outdoors in England.

PLANT DESCRIPTION

Plant:

*Height.*—100 cm.

*Habit.*—Strong and bushy.

Branches:

*Young stems.*—Color: Parrot green 30E8. Texture: Smooth and dull. Thorns: Numerous, variable sizes — basal width 1 mm height 1-9 mm and numerous red glandular hairs.

*Old stems.*—Color: Grass green 30E7 and slightly stripey. Texture: Smooth and dull. Thorns: Numerous, variable sizes — basal width 1-9 mm height 1-9 mm, oxblood red 9E7 and red glandular hairs on some.

LEAVES

Stipules:

*Length.*—1.5-2.2 cm.

*Width.*—5-8 mm.

*Angle of wingtips to petiole.*—45°-80°, wings curved.

*Color.*—30B6.

*Margins.*—Serrate with red tipped glandular hairs.

*Shape.*—Medium width.

Petiole:

*General description.*—Stiff and straight.

*Length.*—9-11 cm.

*Upperside color.*—29E8 deep green.

*Groove/hairs/thorns.*—Groove edged with red glandular hairs.

*Underside.*—30B7 sap green.

*Hair/thorns.*—Thorns 2-8 per internode. Basal width 1-2 cm. Height 1-2 cm and few red glandular hairs.

Leaflets:

*Number.*—3, 5, 7.

*Shape.*—Ovoid, rounded base, slightly cuspidate apex.

*Serration.*—Dentate.

*Texture.*—Tough, leathery, dull — Length 4-8 cm. Width 3-5 cm.

General effect of foliage: Dense — dark green — glossy.

Color:

*Young foliage.*—Upperside: 29F7 braken green. Underside: 29E6 spinach green.

*Adult foliage.*—Upperside: 29F8 dark green. Underside: 29E7/6 dark green Margins: Yellowing slightly.

INFLORESCENCE

Number of flowers per stem: 1-5.

Peduncle:

*Length.*—6-7 cm.

*Color.*—11C6.

*Thorns/hairs.*—Smooth, few red glandular hairs.

Sepals:

*Upperside/color.*—30E8 deep green central longitudinal strip of brownish red 11C8.

*Outer margins.*—1-3 ensiform projections on outer margins.

*Inner margins.*—Lined with fine white downy hairs.

*Underside color.*—30D7 lettuce green.

*Outside and inside texture.*—Leathery and fairly smooth.

*Sepal length.*—3-4 cm.

Bud:

*Shape.*—Rounded with cuspidate apex and pulled into ensiform appendage before bud break.

*Length.*—Variable 3-4.5 cm.

*Max. width.*—1.1-1.8 cm.

*Color when opening.*—11C/08 dark red/wine red.

Flower:

Shape.—Deep cut shape, flattened on top, older flowers doming. Outer petals recurved to stem.

*Diameter.*—8-9 cm.

*Color when opening.*—Upperside: Outer petals: Scarlet 10C8, basal tip yellow 4A5. Underside: Deep red 11C8, basal tip. Pastel 3A4 yellow.

*Color when blooming.*—Upperside: Cerise 12C8 Underside: 12C8 cerise, basal tip 3A3 pale yellow.

*Coloring when finished blooming.*—Upperside: Cerise 12C8.

Underside: 12C8 cerise, basal tip 3A3. Pastel yellow.

Length of blooming season at production location: From June to October.

Fragrance: Sweet, rich, old roses like.

Lasting quality: Good. Range in number of days on plant is 10-14 days. Range in number of days as cut flowers is 8-12 days.

Petals:

*Shape.*—Outside: Irregular, roughly bilobed with, apex rounded and narrowing to truncate base. Max. width 4.5-5.0 cm. Middle: Apex rounded, slightly bilobed and narrowing to truncate base. Max. width 3.0 cm. Inside: Apex rounded, slightly bilobed, narrowing to base, v-shaped with slight shoulder. Max. width 1-2 cm. Inner form petals slightly staminoid.

*Texture.*—Firm, smooth outside — slightly crinkly inside.

*Number.*—76-93 but on average 80.

*Cleaning.*—Good, petals fall quickly to provide a tidy rose.

Stamens:

*Number.*—75-80.

*Anthers.*—Normal, chrome yellow 5A8.

*Filaments.*—Light yellow 3A5, tinged with cerise 12C8 irregular height.

Pistils:

*Number.*—120.

*Stigmas.*—3A4 pastel yellow.

*Styles.*—2A3 pale yellow with fine cerise 12C8 longitudinal.

Receptacle:

*Color.*—11C5.

*Texture.*—Smooth.

*Size.*—7-5 mm.

*Shape.*—Jug shaped.

THE DEVELOPMENT

Vegetation: Vigorous.

Blooming: Abundant and continual.

Aptitude to bearing fruits: None.

Resistance to frost: Good.

Resistance to disease: Very good.

I claim:

1. A new and distinct variety of rose plant of the shrub class, characterized as to novelty by its fully double flowers of scarlet/deep red, with abundant and continual blooming and shaping of the flower being substantially as shown and described.

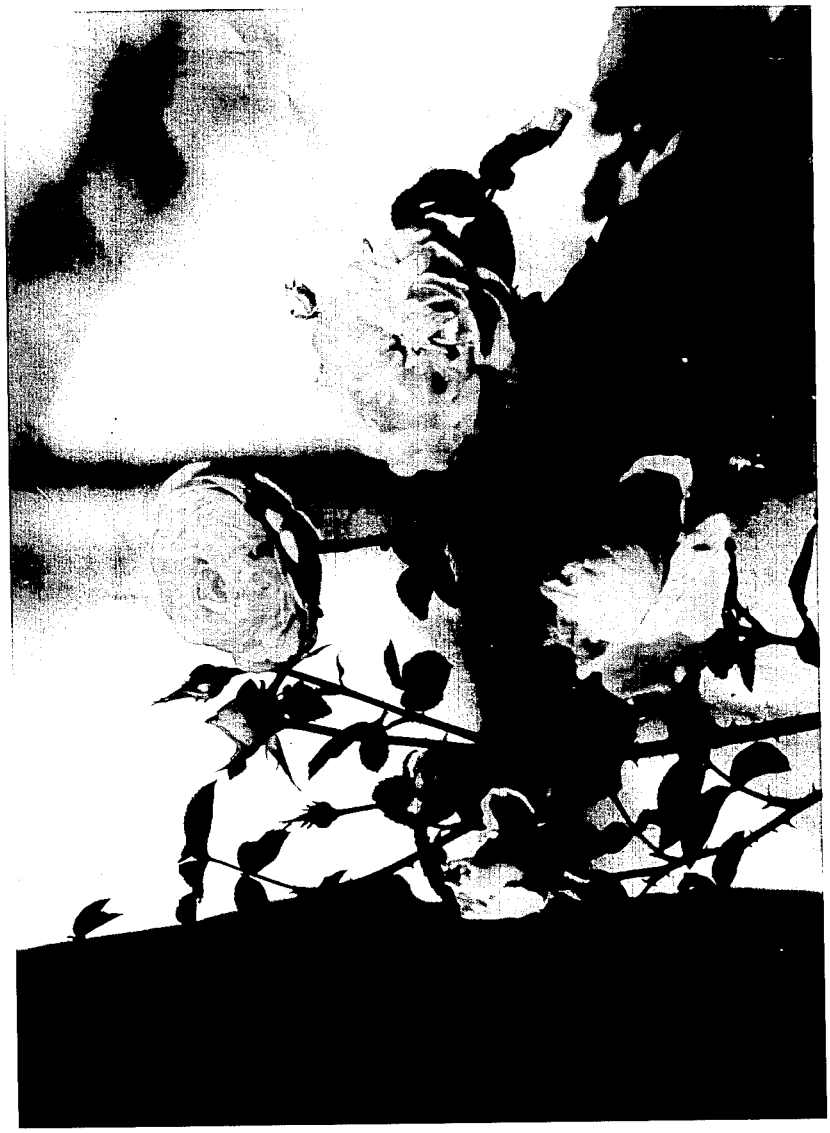

* * * * *